US012208085B2

(12) United States Patent
Manel et al.

(10) Patent No.: US 12,208,085 B2
(45) Date of Patent: Jan. 28, 2025

(54) PYRAZOLINE-DERIVED COMPOUND FOR USE IN THE PREVENTION AND/OR TREATMENT OF PAIN AND INFLAMMATION ASSOCIATED TO SURGERY IN MAMMALS

(71) Applicant: ECUPHAR NV, Oostkamp (BE)

(72) Inventors: Homedes Beguer Josep Manel, Barcelona (ES); Salichs Florensa Marta, Barcelona (ES)

(73) Assignee: ECUPHAR NV (BE)

( * ) Notice: Subject to any disclaimer, the term of this patent is extended or adjusted under 35 U.S.C. 154(b) by 0 days.

(21) Appl. No.: 17/828,297

(22) Filed: May 31, 2022

(65) Prior Publication Data

US 2023/0381140 A1 Nov. 30, 2023

(51) Int. Cl.
*A61K 31/415* (2006.01)
*A61P 29/00* (2006.01)

(52) U.S. Cl.
CPC ............ *A61K 31/415* (2013.01); *A61P 29/00* (2018.01)

(58) Field of Classification Search
CPC ............................... A61K 31/415; A61P 29/00
See application file for complete search history.

(56) References Cited

U.S. PATENT DOCUMENTS 6,353,117 B1 * 3/2002 Cuberes-Altisent .... A61P 17/06
548/379.7

FOREIGN PATENT DOCUMENTS

| EP | 1083171 B1 | 4/2004 | |
|---|---|---|---|
| EP | 3009137 A1 | 4/2016 | |
| WO | WO-2004017952 A1 * | 3/2004 | ........... A61K 31/075 |
| WO | WO-2005025510 A2 * | 3/2005 | ............. A61K 31/34 |

OTHER PUBLICATIONS

Reinoso et al (Journal of Pharmaceutical and Biomedical Analysis, 2001; 24(5-6):897-911) (Year: 2001).*
Homedes et al.(Journal of Veterinary Pharmacology and Therapeutics, 2021; 44(6):888-901, published online Jun. 23, 2021) (Year: 2021).*
Mathews KA. Pain assessment and general approach to management. Vet Clin North Am Small Anim Pract. Jul. 2000;30(4):729-55.
Pascoe PJ. Perioperative pain management. Vet Clin North Am Small Anim Pract. Jul. 2000;30(4):917-32.
Bonnet F, Marret E. Influence of anaesthetic and analgesic techniques on outcome after surgery. Br J Anaesth. Jul. 2005; 95(1):52-8. doi: 10.1093/bja/aei038. Epub 2004.
Wagner AE, Worland GA, Glawe JC, Hellyer PW. Multicenter, randomized controlled trial of pain-related behaviors following routine neutering in dogs. J Am Vet Med Assoc. Jul. 1, 2008;233(1):109-15.

Lamont LA, Mathews KA. Opioids, non-steroidal anti-inflammatoires and analgesic adjuvants. In: Tranquilli WJ, Thurmon JC, Grimm KA, eds. Lumb and Jones' Veterinary Anesthesia and Analgesia. 4th edn. Blackwell Publishing, 2007:241-72.
Budsberg SC, Cross AR, Quandt JE, Pablo LS, Runk AR. Evaluation of intravenous administration of meloxicam for perioperative pain management following stifle joint surgery in dogs. Am J Vet Res. Nov. 2002; 63(11):1557-63. doi: 10.2460/ajvr.2002.63.1557. PMID: 12428667.
Martins TL, Kahvegian MA, Noel-Morgan J, Leon-Roman MA, Otsuki DA, Fantoni DT. Comparison of the effects of tramadol, codeine, and ketoprofen alone or in combination on postoperative pain and on concentrations of blood glucose, serum cortisol, and serum interleukin-6 in dogs undergoing maxillectomy or mandibulectomy. Am J Vet Res. Sep. 2010;71(9):1019-26.
Kerr, C. (2016) Pain management I: systemic analgesics In: BSAVA Manual of Canine & Feline Anaesthesia & Analgesia. 2nd ed. Eds C. J. Seymour and T. Duke-Novakowski. BSAVA, Gloucester, UK. Chapter 10, pp. 124-142.
Gruet P, Seewald W, King JN. Evaluation of subcutaneous and oral administration of robenacoxib and meloxicam for the treatment of acute pain and inflammation associated with orthopedic surgery in dogs. Am J Vet Res. Feb. 2011;72(2):184-93. doi: 10.2460/ajvr.72.2.184. PMID: 21281192.
Friton G, Thompson CM, Karadzovska D, King S, King JN. Efficacy and safety of oral robenacoxib (tablet) for the treatment of pain associated with soft tissue surgery in client-owned dogs. BMC Vet Res. Jun. 26, 2017;13(1):197.
Grandemange E, Fournel S, Woehrlé F. Efficacy and safety of cimicoxib in the control of perioperative pain in dogs. J Small Anim Pract. Jun. 2013;54(6):304-12.
Ramirez J, Barthélémy N, Noël S, Claeys S, Etchepareborde S, Farnir F, Balligand M. Complications and outcome of a new modified Maquet technique for treatment of cranial cruciate ligament rupture in 82 dogs. Vet Comp Orthop Traumatol. 2015;28(5):339-46.
Reid J, Nolan AM, Hughes JML, et al. Development of the short-form Glasgow Composite Measure Pain Scale (CMPSSF) and derivation of an analgesic intervention score. Animal Welfare 2007;16(S):97-104.
Selective inhibition of cyclooxygenase-2 by enflicoxib, its enantiomers and its main metabolites in vitro in canine blood. Solà J, Menargues À, Homedes J, Salichs M, Álvarez I, Romero L, Vela JM. J Vet Pharmacol Ther. May 2022;45(3):235-244. doi: 10.1111/jvp.13042. Epub Jan. 17, 2022.
Comparative In vitro Metabolism of Enflicoxib in Dogs, Rats, and Humans: Main Metabolites and Proposed Metabolic Pathways. Solà J, Menargues À, Homedes J, Salichs M, Serafini MT, Encina G. Drug Metab Lett. 2021;14(3):206-218. doi: 10.2174/1872312814666211209161933.
Pharmacology of enflicoxib, a new coxib drug: Efficacy and dose determination by clinical and pharmacokinetic-guided approach for the treatment of osteoarthritis in dogs based on an acute arthritis induction model. Cendrós JM, Salichs M, Encina G, Vela JM, Homedes JM. Vet Med Sci. Jan. 2022;8(1):31-45. doi: 10.1002/vms3.670. Epub Dec. 2, 2021.
Efficacy and safety of enflicoxib for treatment of canine osteoarthritis: A 6-week randomised, controlled, blind, multicentre clinical trial. Salichs M, Badiella L, Sarasola P, Homedes J. Vet Rec. Sep. 29, 2021:e949. doi: 10.1002/vetr.949. Online ahead of print. PMID: 34590318.

(Continued)

*Primary Examiner* — Rayna Rodriguez
(74) *Attorney, Agent, or Firm* — Shackelford, McKinley & Norton, LLP

(57) ABSTRACT

The present invention relates to a method of treating or preventing pain and inflammation associated to surgery in a mammal by administering the compound E-6087 to the mammal.

16 Claims, 9 Drawing Sheets

(56) References Cited

OTHER PUBLICATIONS

Pharmacokinetics of enflicoxib in dogs: Effects of prandial state and repeated administration. Homedes J, Salichs M, Solà J, Menargues A, Cendrós JM, Encina G. J Vet Pharmacol Ther. Nov. 2021;44(6):888-901. doi: 10.1111/jvp.12995. Epub Jun. 23, 2021. PMID: 34160092.

Long-term safety evaluation of Daxocox® tablets (enflicoxib) in dogs after weekly oral administrations for seven months. Homedes J, Salichs M, Guzman A. BMC Vet Res. Jun. 3, 2021;17(1):205. doi: 10.1186/s12917-021-02910-0. PMID: 34082759 Free PMC article.

Reinoso et al., "Pharmacokinetics of E-6087, a New Anti-inflammatory Agent, in Rats and Dogs", Biophann. Drug Dispos. 22: 231-242 (2001).

Cendrós JM, Salichs M, Encina G, Vela JM, Homedes JM. "Pharmacology of enflicoxib, a new coxib drug: Efficacy and dose determination by clinical and pharmacokinetic-guided approach for the treatment of osteoarthritis in dogs based on an acute arthritis induction model." Vet Med Sci. Jan. 2022;8(1):31-45.

Evaluation of the Genotoxic Potential of the Selective COX-2 Inhibitor Enflicoxib in a Battery of in vitro and in vivo Genotoxicity Assays. Guzmán A, Homedes J, Salichs M. Drug Res (Stuttg). Mar. 2022;72(3):163-170. doi: 10.1055/a-1727-5733. Epub Jan. 18, 2022. [NPL 14].

* cited by examiner

PYRAZOLINE-DERIVED COMPOUND FOR USE IN THE PREVENTION AND/OR TREATMENT OF PAIN AND INFLAMMATION ASSOCIATED TO SURGERY IN MAMMALS

FIELD OF THE INVENTION

The present invention relates to a pyrazoline-derived compound for use in the prevention and/or treatment of pain and inflammation associated to surgery procedures in mammals. In particular, the invention refers to the COX-2 selectively blocking compound E-6087. The present invention relates to the treatment of mammals, preferably dogs.

BACKGROUND OF THE INVENTION

Postoperative pain is often the predominant symptom after a surgical procedure. Without an effective control of postoperative pain, animals can suffer undesirable effects such as loss of appetite, self-trauma of the surgical site, maladaptive physiological responses or maladaptive behaviours, which increase the recovery time (1, 2). The relief of pain in the perioperative period prevents from postoperative complications, improving the recovery and comfort of the animals undergoing surgical procedures (3, 4). There are three main analgesic groups in veterinary medicine that are used to treat perioperative pain: opioids, nonsteroidal anti-inflammatory drugs (NSAIDs) and local anaesthetics.

NSAIDs are usually used to control acute pain from surgery or may be administered in chronic situations, for example, to relieve osteoarthritis-related pain (5). It is common to combine opioids with NSAIDs and this combination appears to be more effective for postoperative pain control than the use of opioids alone (6, 7). NSAIDs offer some advantages over opioids: long duration of effect; anti-inflammatory properties; lack of behaviour-modifying effects, no respiratory and cardiovascular side effects; availability of oral formulations and no regulatory control. All this makes them an optimal choice for acute and chronic pain treatment in veterinary medicine (8). However, disadvantages include the absence of antagonist agents and the possibility of producing gastrointestinal side effects, kidney injury, blood coagulation abnormalities, liver injury and possible cartilage injury with chronic use.

NSAIDs are acidic anti-inflammatory agents that inhibit the enzyme cyclooxygenase (COX) which catalyses the conversion of arachidonic acid to prostaglandins and thromboxane. Advances in the early 1990s showed the presence of two isoforms of COX, namely COX-1 and COX-2.

On the one hand, COX-1 is the constitutive form as it produces prostaglandins that are important for normal physiological function and are produced by many tissues, including gastrointestinal cells, platelets, endothelial cells and renal cells. On the other hand, COX-2 is an inducible form of the enzyme, the expression of which is tightly controlled under basal conditions but is dramatically up regulated in the presence of inflammation. Proinflammatory cytokines are known to stimulate the expression of COX-2 in many cells, including synovial cells, endothelial cells, chondrocytes, osteoblasts, monocytes and macrophages. Indeed, synovial and subchondral bone tissue from hips of dogs with osteoarthritis have been shown to present increased COX-2 expression compared with healthy dogs.

The main mechanism of action of most NSAID's is the blocking of prostaglandin synthesis by non-selectively binding to and inhibiting the action of the COX-1 and COX-2 isoenzymes. The major therapeutic and toxic effects of NSAIDs are associated with this mechanism.

During the last decades, a new class of NSAID's, the coxibs, has been developed. The coxibs bind more selectively to the isoenzyme COX-2, allowing the aimed therapeutic effects without the common side effects related to COX-1 inhibition. Firocoxib (Previcox®), Robenacoxib (Onsior®), Deracoxib (Deramaxx®) and Cimicoxib (Cimalgex®) are the currently licensed Coxibs in Europe and/or the USA for the control of postoperative pain in dogs. There are also scientific publications evaluating the efficacy of coxibs in controlling acute postoperative pain in dogs undergoing orthopaedic or soft tissue surgery (9, 10, 11).

The treatment of postoperative pain in mammals and particularly in companion animals like dogs has traditionally been performed with daily oral administration of NSAIDs. The oral administration of medicines in companion animals contrary to humans has mainly two problems related to treatment compliance. The first is the acceptance of the medication by the animal. To solve this, formulations with aroma have been developed in order to increase the animal voluntary acceptance and facilitate oral intake. The second problem is that daily administration is subjected to very close supervision of treatment by the person administering the medicine to the animal. It is frequent that owners miss the administration of some doses, either due to an oversight or because it is complicated to administer the product every day for different reasons (aggressive animals, outdoor housed animals, etc). All this will end up in loss of treatment compliance that may result in lack of efficacy or incomplete efficacy.

Thus, there is a need to develop medicines that avoid these disadvantages with less frequent administrations to the animal in order to improve treatment compliance assuring animal welfare. The present invention could solve the above-mentioned problem using the long-lasting compound E-6087.

E-6087 was first disclosed in EP1083171, where its anti-inflammatory activity in rats was taught. It has also been disclosed in EP3009137A1, where a weekly treatment to control pain and inflammation associated to osteoarthritis in dogs was described. However, these documents are silent about any posology for the prevention and/or treatment of post-operative pain and inflammation.

SUMMARY OF THE INVENTION

In an embodiment, the present invention relates to a compound of formula (I):

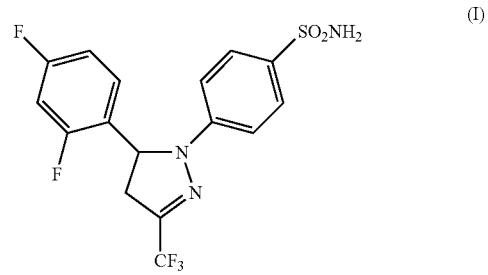 [SMILES: NS(=O)(=O)c1ccc(N2N=C(C(F)(F)F)CC2c2ccc(F)cc2F)cc1]

also named herein as "E-6087" or known as "enflicoxib", for use in the prevention and/or treatment of pain and inflammation associated to surgery in mammals.

In an embodiment, the present invention relates to a method of treating or preventing pain and inflammation associated to surgery in a mammal by administering to said mammal a compound of formula (I).

DETAILED DESCRIPTION OF THE INVENTION

Figure 1:
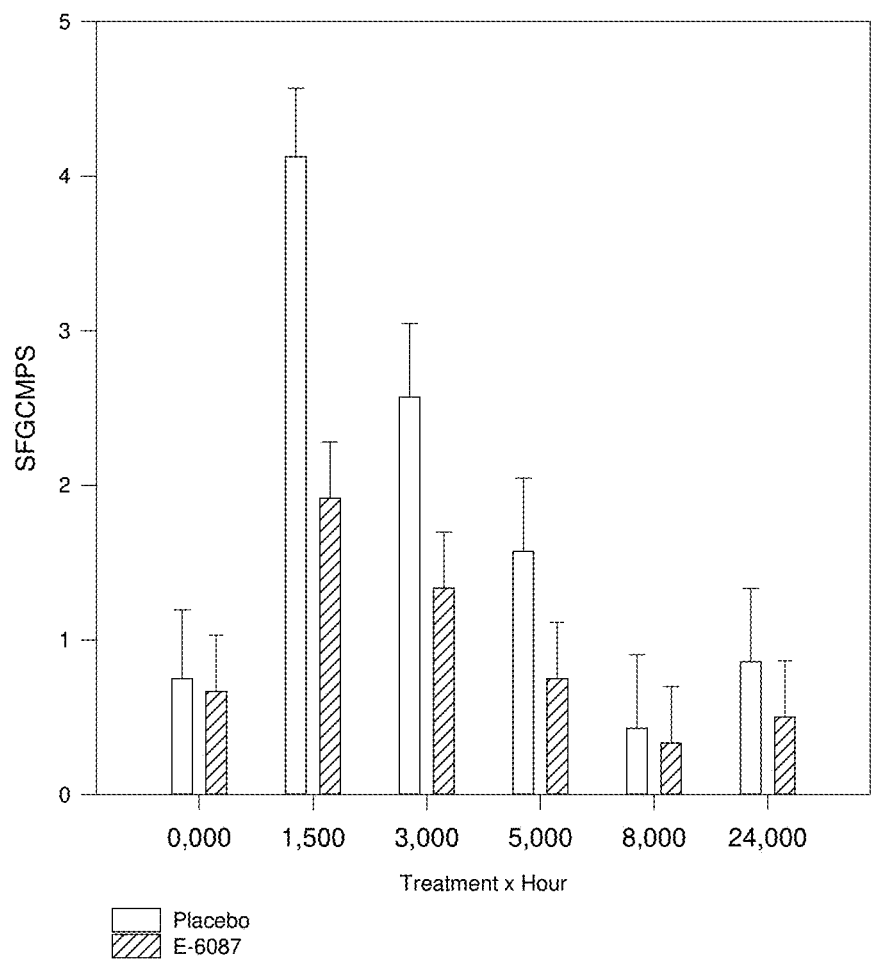
FIG. 1. Evolution of average SFGMPS total scores at the different time points after soft tissue surgery in dogs treated with E-6087 or Placebo.

The present invention relates to a compound of formula (I):

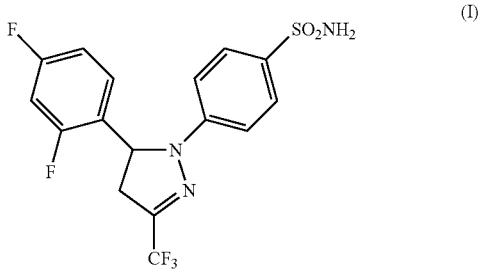 [SMILES: NS(=O)(=O)c1ccc(N2N=C(C(F)(F)F)CC2c2ccc(F)cc2F)cc1]

(I)

for use in the prevention and/or treatment of pain and inflammation associated to surgery in mammals.

Alternatively, the present invention relates to a method of preventing and/or treating pain and inflammation associated to surgery, comprising administering to said mammal the compound of formula (I). In an embodiment, the compound may be administered to a mammal in need thereof. In an embodiment, the compound may be administered at a therapeutically effective amount. By "therapeutically effective amount" is intended to mean in the context of the present invention an effective amount, in the doses and for the periods of time as necessary, to achieve the desired prophylactic/therapeutic result.

Alternatively, the present invention relates to the use of the compound of formula (I) for manufacturing a medicament for the prevention and/or treatment of pain and inflammation associated to surgery in mammals. Alternatively, the present invention relates to methods of manufacturing a medicament that includes the compound of formula (I).

Unless otherwise explained, all technical and scientific terms used herein have the same meaning as commonly understood by one of ordinary skill in the art to which this disclosure belongs. The singular terms "a", "an", "one" and "the" include plural referents unless context clearly indicates otherwise. Similarly, the word "or" is intended to include "and" unless the context clearly indicate otherwise.

As mentioned before, the compound of formula (I) is also named as E-6087 or enflicoxib.

As used herein, the terms "preventing", "prevent" or "prevention" includes prophylaxis of the pain and inflammation associated to surgery, or alleviation of the symptoms associated thereto symptoms.

As used herein, the terms "treating", "treat" or "treatment" includes a therapeutic action over the pain and inflammation associated to surgery, or alleviation of the symptoms associated thereto symptoms, whose pain and inflammation or symptoms associated thereto are already being suffered by the mammal.

As used herein "preventing" or "treating" does not exclude that both actions "preventing" and "treating" can be carried out on the same mammal.

In a preferred embodiment, said prevention and/or treatment comprises administering the compound at a single dose from 1 to 10 mg/kg of body weight, i.e., for example, 1, 2, 3, 4, 5, 6, 7, 8, 9, 10 mg/kg of body weight or any amount comprised in said range.

Unless otherwise specified, the therapeutic dose will always refer to mg of active product per kg of body weight (or mg/kg).

In a further preferred embodiment, the dose is from 4 to 8 mg/kg of body weight, including any amount comprised in said range.

In an even further preferred embodiment, the dose is 4 mg/kg of body weight.

In an even further preferred embodiment, the dose is 8 mg/kg of body weight.

In the context of the present invention, "surgery" refers to those medical procedures involving an incision with instruments, performed to repair damage or arrest a disease or any other beneficial action over a living body due to several medical reasons, such as a castration or ovariohysterectomy. In the veterinary field, surgery procedures usually fall into three broad categories: orthopaedic surgeries (bones, joints, muscles), soft tissue surgeries (skin, body cavities, cardiovascular system, gastrointestinal/urogenital/respiratory tracts), and neurosurgery. Preferred embodiments and examples of surgeries considered in the present invention are mentioned below.

In a preferred embodiment, said surgery is a soft tissue surgery.

Soft tissue surgeries include, but are not limited to: Total ear canal ablation (TECA); bulla osteotomy; Tumours of the face and mouth; Reconstructive surgery; Salivary mucocele; Tumours of the neck (thyroid, parathyroid, salivary glands and surrounding soft tissues; tie back procedure for laryngeal paralysis; stenotic nares; palate trim for elongated soft palate); Tumours of the torso and extremities; Spleen and liver tumours; Body wall reconstruction for tumours, hernias and trauma; Mastectomy; Removal of gall bladder for obstruction, gall stones, tumours and mucocele; Removal of kidney for Tumours, obstruction or trauma; Tumours of the urinary bladder, prepuce, penis, scrotum and vulva; Perineal urethrostomy; Recessed vulva; Anal gland removal, Ovariohysterectomy Cryptorchidectomy, Cystotomy, Splenectomy, Gastropexy, Caesarean section, Ovariectomy, Gastrointestinal, Genitourinary and Thoracic surgeries.

In another preferred embodiment, said surgery is an orthopaedic surgery.

Orthopaedic surgeries include, but are not limited to: Tibial plateau leveling osteotomy (TPLO); Lateral stabilization suture (LSS); Medial patellar luxation (MPL); Lateral patellar luxation (LPL); Fractures of the radius and ulna; Fractures of the metacarpal and metatarsal; Fractures of the femur; Fractures of the tibia; Femoral head and neck osteotomy (FHO); Open hip reduction using toggle; OCD of the shoulder; OCD of the hock; Fragmented coronoid process of the elbow (FCP); Un-united anconeal process of the elbow (UAP); Pancarpal arthrodesis; Partial carpal arthrodesis; Pantarsal arthrodesis; Limb-sparing for osteosarcoma; Amputation of Limb, Arthroscopy, Ulna osteotomy and Hemi-pelvectomy.

In another preferred embodiment, said surgery is a neurosurgery.

Neurosurgeries include, but are not limited to: Complex/refractory seizures; Immune-mediated diseases, such as Myasthenia Gravis, Polymyositis/polyneuropathy or Optic neuritis; Inflammatory and infectious diseases of the brain, spine, and spinal cord, such as Granulomatous meningoencephalitis (GME), Meningoencephalomyelitis of unknown aetiology (MUE), Diskospondylitis; Stroke; Metabolic disease or Disc disease.

In another preferred embodiment, said surgery is a dental surgery.

In another preferred embodiment, said surgery is an oncologic surgery.

In another preferred embodiment, said surgery is an ear surgery.

In another preferred embodiment, said surgery is a skin tumour removal surgery.

Regarding the posology, in a preferred embodiment, the single dose is administered at least 2 days before the surgery, 1 day before the surgery, the same day of the surgery or one day after the surgery. It was experimentally shown (see example section) that a single dose preferably 1 day before surgery was capable to control pain and inflammation associated to orthopaedic surgery (TPLO) during the follow up of the study (10 days).

The posology described in the present invention has the advantage of being very easy, facilitating thereby the adhesion to treatment (treatment compliance) with a good margin of safety compared to other already available NSAIDs to be administered daily.

Although the compound of formula (I) can be used for the treatment of pain and inflammation associated to surgery in any kind of mammals following the above-mentioned posology, it is preferably useful in dogs.

In another preferred embodiment, the compound of formula (I) for use according to any of the embodiments disclosed herein is included in a composition, preferably a pharmaceutical composition, with at least one pharmaceutically acceptable excipient.

Such excipients can be selected among carriers, support materials, lubricants, fillers, solvents, diluents, colorants, flavour conditioners such as sugars, antioxidants and/or binders. In the case of suppositories, this may involve waxes or fatty acid esters or preservatives, emulsifiers and/or carriers for parenteral application. The selection of excipients and additives and the amounts to be used will depend how the pharmaceutical composition is to be administered.

The pharmaceutical composition in accordance with the invention can be adapted to any route of administration, oral or parenteral, for example pulmonary, nasal, rectal, subcutaneously, intramuscularly and/or intravenously.

Preferably, the composition is suitable for the oral administration.

Suitable formulations for oral administration may be tablets, including chewing tablets, capsules, chewing gums, powders, drops, gels, juices, syrups, solutions and suspensions. It may also be in the form of multiparticulates, preferably microparticles, microtablets, pellets or granules, optionally compressed into a tablet, filled into a capsule or suspended in a suitable liquid. Suitable liquids are known to those skilled in the art.

Suitable formulations for parenteral administration may be solutions, suspensions, dry powder to reconstitute preparations or sprays.

The compounds of the invention can be formulated as deposits in dissolved form or in patches, for percutaneous administration.

Skin applications include ointments, gels, creams, lotions, suspensions or emulsions.

The preferred form of rectal application is by means of suppositories.

The composition according to the present invention may be produced following standard procedures known to those skilled in the art.

In an embodiment, the present invention pertains to a method of treating or preventing pain and inflammation associated to surgery in a mammal by administering to said mammal a compound of formula (I). In an embodiment, the administering includes administering the compound at a single dose from 1 to 10 mg/kg of body weight. In an embodiment, the dose is from 4 to 8 mg/kg of body weight. In an embodiment, the dose is 4 mg/kg or 8 mg/kg of body weight.

In an embodiment, the surgery is a soft tissue surgery. In an embodiment, the surgery is an orthopaedic surgery. In an embodiment, the surgery is a neurosurgery. In an embodiment, the surgery is a dental surgery. In an embodiment, the surgery is an oncologic surgery. In an embodiment, the surgery is an ear surgery. In an embodiment, the surgery is a skin tumour removal surgery.

In an embodiment, the single dose is administered at least 2 days before the surgery. In an embodiment, the single dose is administered at least 1 day before the surgery. In an embodiment, the single dose is administered at least the same day of the surgery. In an embodiment, the single dose is administered at least one day after the surgery.

In an embodiment, the mammal is a dog. In an embodiment, the compound is included in a composition with at least one pharmaceutically acceptable excipient.

In an embodiment, the method treats said pain and inflammation. In an embodiment, the method prevents said pain and inflammation. In an embodiment, the method treats and prevents said pain and inflammation.

It is noted that any of the embodiments disclosed herein for the compound or the composition can be taken alone or combined with any other embodiment disclosed herein unless the context specifies otherwise. In other words, for example, a preferred option of a defined feature can be combined with a more or less preferred option of another feature.

Described below are several examples by way of illustration of the invention and do not limit it in anyway.

EXAMPLES

Example 1: Efficacy of E-6087 in the Control of Postoperative Pain and Inflammation in Dogs Undergoing Experimental Orthopaedic Surgery The study was performed with 6 clinically healthy Beagle dogs with similar age and weight that were experimentally subjected to knee surgery (repair of cranial cruciate ligament rupture). Five dogs were treated with E-6087 as test product (TP) and acted as treated group (TG) while one dog was treated with meloxicam as reference product (RP) and acted as positive control group (CG). All surgeries were conducted under the same preoperative, intraoperative and postoperative protocols and performed by the same surgeon. A highly standardized surgical technique, Maquet Modified Procedure (MMP) (12) was implemented.

For each dog the study lasted 17 days, including a 7-day acclimatization period. On day D−1 (approximately 24 h before the intervention) the five dogs in the TG received a single oral dose (8 mg/kg) of the TP, the one dog in the CG received a single subcutaneous dose (0.1 mg/kg) of the RP. Meloxicam administration was repeated on D0 before surgery, and every 24 h post-surgery up to day D7. On day D0 all dogs underwent knee surgery in the right knee. From day D1 up to day D10 dogs were closely examined and signs of pain and discomfort were blindly evaluated and rated using the Short Form of the Glasgow Composite Pain Scale (SFGCPS) ranging from 0 to 24 (13 and http://www.new-metrica.com/cmps/). On day D−1 dogs were also examined to rule out signs of pain or discomfort.

The product E-6087 has shown to be effective as analgesic agent in the postoperative period after orthopaedic surgery. None of the animals needed rescue analgesia during the 10 days follow up period. No potential adverse effects related to product administration were recorded.

According to the good safety and efficacy profile observed in this study, E-6087 seems to be a good candidate for further clinical development in the control of postoperative pain.

Example 2: Efficacy of E-6087 in the Control of Postoperative Pain and Inflammation in Dogs Undergoing Soft Tissue Surgery The study was a single centre, prospective, parallel-controlled, randomized and blinded pilot field trial with a negative (Placebo) control to evaluate the efficacy of E-6087 in dogs undergoing elective soft tissue surgery.

Twenty dogs (17 females and 3 males) were included in the study. Dogs were of different breeds or crossbreed, ages from 3 months to 7 years and weights from 4 to 34 kg. All dogs were clinically healthy other than the condition causing the animal to go under surgery.

Two days before surgery animals were weighed, a detailed physical examination was performed, and blood samples were collected for routine haematology and biochemistry to confirm the good health status of the animals before inclusion.

Dogs were randomly allocated to receive either E-6087 or Placebo as oral tablets. E-6087 and Placebo tablets were similar (same appearance and packaging), therefore treatment administration, clinical examinations and blood sample analysis was always blind.

E-6087 was administered at the dose of 8 mg/kg on day D−1, approximately 24 h before surgery scheduled time, before the first meal of the day. Placebo tablets were administered following the same posology.

Surgeries were performed in the morning, on day D0 by the Investigator (Surgeon). All surgeries were performed under the same anaesthesia protocol. Premedication was performed with medetomidine and morphine both at 0.1 ml/10 kg followed by anaesthesia maintained with Tiletamine/Zolazepam (Zoletil®). Local anaesthesia was not permitted. At the end of surgery, antibiotic therapy was administered to all dogs following the post-operative protocol stablished: amoxicillin (trihydrate) at 15 mg of amoxicillin/kg bw in a single dose.

Clinical assessments of postoperative pain and inflammation were done by the Investigator (Examining Veterinarian) using the SFGCMPS (13). Visual Analog Scales (VAS) were also used to assess pain at rest and under palpation as well as the level of inflammation.

On D0 at approximately 2 hours before surgery the Examining Veterinarian performed a physical examination and the clinical assessment of pain and inflammation to determine the basal scores. After surgery pain and inflammation were assessed at six examination time points: t1.5 h, t3 h, t5 h (±30 minutes), t8 h (±1 hour), t24 h and t168 (D7), when t0 h corresponded to the end of surgery (extubation).

Clinical assessment of pain and inflammation included assessments of vocalization, attention to wound area, mobility, reaction to pressure at the wound area, general behaviour as well as activity and posture as per SFGCMPS. In addition, pain at rest and after palpation as well as the level of inflammation were assessed at the same time points by VAS ranging from 0 (no pain) to 100 (severe pain manifested by vocalization, aggression, and refusal to allow examination) and from 0 (no inflammation) to 100 (major inflammation as local heat, redness or paresis of the affected area).

Statistical Analysis was performed by use of commercially available software (SigmaPlot for Windows version 13.0). The area under the curve (AUC) was calculated for observable pain during the initial 8 and 24 hours, and it was considered as the primary efficacy variable. All analyses applied a two-sided significance level $\alpha=0.05$ and a power $\beta=80\%$. Demographic and baseline data were compared using the Mann-Whitney U test. Gender was compared with the Fisher exact probability test in contingency tables. Efficacy variables were analysed by repeated measures ANOVA.

The foremost surgical procedure was ovariohysterectomy, and this determined that most included animals were females. Sixteen females were ovariohysterectomized. Two males were castrated by cryptorchidectomy. One male had a perianal hernia and one female was ovariectomized and had an umbilical hernia. All surgeries lasted less than 30 minutes except for one that lasted 54 minutes (perineal hernia).

A statistical analysis was performed to confirm both groups were balanced for the main variables before surgery (see Table 1).

TABLE 1

Homogeneity distribution between treatments before surgery

|  | Placebo | E-6087 | P |  |
| --- | --- | --- | --- | --- |
| Males | 1 | 2 | 1.00 | NS |
| Females | 7 | 10 |  |  |
| Body weight (kg) | 17.06 ± 8.61 (9.5-32) | 18.05 ± 10.19 (4-34) | 0.91 | NS |
| SFGCMPS | 0.75 | 0.67 | 0.446 | NS |
| Pain at rest | 0.037 | 0 | 0.261 | NS |
| Pain after palpation | 0.025 | 0.008 | 0.767 | NS |
| Inflammation | 0 | 0.008 | 0.47 | NS |

These results confirmed that both treatment groups were homogeneous and balanced for all parameters and variables before surgery. Blood analyses results revealed all parameters to be within the reference range. All clinical examinations were performed except for seven dogs that were lost for follow up after the 5 h examinations and no data for these dogs could be recorded at 8 h and beyond.

Although values of AUC (primary efficacy variable) for the first 24 hours after surgery were almost half in the dogs treated with E-6087, this difference did not reach statistical significance (p=0.266). However, when considering the AUC for the first 8 hours, dogs treated with E-6087 had statistically significant lower values (p=0.033) (see Table 2).

TABLE 2

SFGCMPS average values at 1.5, 3, 5, 8, and 24 hours after surgery in both treatment groups.

|  | Placebo | | | | | E-6087 | | | | |
| --- | --- | --- | --- | --- | --- | --- | --- | --- | --- | --- |
|  | 1.5 h | 3 h | 5 h | 8 h | 24 h | 1.5 h | 3 h | 5 h | 8 h | 24 h |
| Vocalization | 0.25 | 0.38 | 0.25 | 0 | 0 | 0.25 | 0.25 | 0 | 0 | 0 |
| Attention to wound | 0 | 0.25 | 0.25 | 0 | 0.13 | 0 | 0.08 | 0.08 | 0 | 0 |
| Mobility | 1.38 | 0.88 | 0.13 | 0.25 | 0.13 | 0.33 | 0 | 0 | 0 | 0 |
| Pressure on wound | 0.38 | 0.50 | 0.88 | 1 | 1 | 0.33 | 0.42 | 0.50 | 0.67 | 0.50 |
| Demeanour | 1.63 | 0.88 | 0.50 | 0.25 | 0.25 | 0.83 | 0.50 | 0.17 | 0 | 0 |
| Posture/Activity | 0.50 | 0.38 | 0.25 | 0.50 | 0.25 | 0.17 | 0.08 | 0 | 0 | 0 |
| Total SFGCMPS | 4.13 | 3.25 | 2.25 | 2 | 1.75 | 1.92 | 1.33 | 0.75 | 0.50 | 0.50 |
| $AUC_{0 \to 24\,h}$ | 25.9 ± 23 | | | | | 16.0 ± 15 | | | | |
| $AUC_{0 \to 8\,h}$ | 13.9 ± 6.3 | | | | | 8.0 ± 5.0 | | | | |

Total scores for SFGCMPS (secondary efficacy variable) at each time point were always lower for E-6087, although differences were statistically significant only at 1.5, 3 and 5 hours (p<0.001, 0.007 and 0.042 respectively) after surgery (see FIG. 1).

Additionally, no differences were detected in vocalization or attention and pressure to wound at any time point. However, statistically significant differences were seen in mobility at 1.5- and 3-hour post-surgery (P<0.0001) and demeanour and posture at 1.5 h (P=0.01, and 0.023 respectively).

Figure 2:
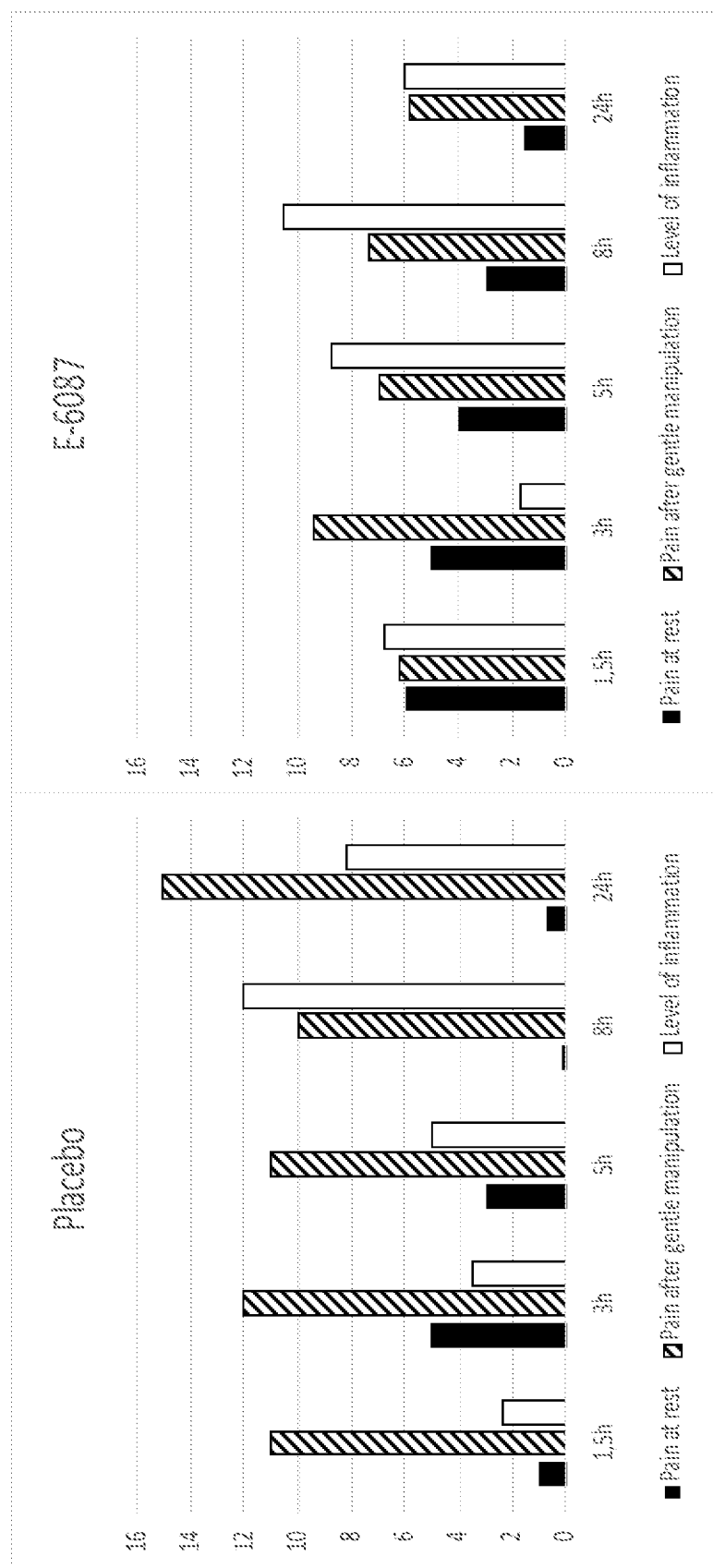
FIG. 2. Evolution of average pain at rest, pain after manipulation and level of inflammation scores at the different time points after soft tissue surgery in dogs treated with E-6087 or Placebo.

No statistically significant differences were detected at any time point for the secondary efficacy variables pain at rest or after palpation. However, analysis for the level of inflammation revealed statistically significant differences at 3 hours after surgery (p=0.021), were the level of inflammation for the group treated with Placebo was greater than for the group treated with E-6087. (See FIG. 2)

No adverse events were observed in any of the included animals during the whole study.

In conclusion, this study allows to conclude that a single dose of 8 mg/kg of E-6087 is effective in alleviating pain and inflammation after soft tissue surgery.

Example 3: Efficacy of E-6087 in the Control of Postoperative Pain and Inflammation in Dogs Undergoing Orthopaedic Surgery The study was a non-inferiority, multicentre, prospective, parallel-controlled, randomized and blinded field study.

Thirty-two dogs of different breed, age and weight presenting at the veterinary practice for orthopaedic surgery were included. Sixteen dogs were treated with E-6087 (Treated Group—TG) while the other sixteen were treated with meloxicam (Positive Control Group—CG) as reference product. E-6087 was administered as oral tablets at the dose of 8 mg/kg the day before surgery (D−1). Meloxicam was administered subcutaneous or intravenously at the dose of 0.2 mg/kg (equivalent to 0.4 mL/10 kg) on day D0 just before surgery (at the time of anaesthesia induction). Meloxicam administration was repeated every 24 h post-surgery, from D1 to D7 (168 h) by oral route (oral suspension or oral tablets) at the dose of 0.1 mg/kg (equivalent to 0.2 mL/10 kg).

Agents with analgesic effect were permitted as premedication. However, intraoperative or postoperative analgesia were not permitted.

For each dog the study lasted twelve days. Two days before surgery, all animals were weighed and underwent a thorough physical examination with clinical pathology to confirm the good health status of the animals before inclusion. Day 0 (D0) was the day dogs underwent surgery and t0 h corresponded to the end of surgery (extubation). The physical examination was repeated on D0, before surgery (t−2 h) and before dispatch (t8 h) and again at t24 h (D1) and t168 (D7) post-surgery. Clinical assessments of pain and inflammation were blindly performed on D0, before surgery (t−2 h) and again at t1.5 h, t3 h, t5 h, t8 h, t24 h (D1) and t168 h (D7) post-surgery. The global efficacy of treatments was assessed on D7. From day D1 to day D7 post-surgery, the owners assessed the dog's wellbeing.

The primary endpoint for efficacy comprises the sum of scores for the SFGCMPS scale, which was assessed at different time points by the Investigator.

The investigator also assessed four secondary efficacy endpoints at the same time points:

Pain at rest by use of a VAS ranging from 0 (no pain) to 100 (severe pain manifested by vocalization, aggression, and refusal to allow examination).

Pain during gentle palpation or manipulation of the affected limb or joint by use of a VAS ranging from 0 (no pain elicited) to 100 (severe pain manifested by vocalization, aggression, and refusal to allow examination).

Level of inflammation based on swelling of the affected joint or limb, local heat, redness, or paresis by use of a VAS ranging from 0 (no inflammation) to 100 (major inflammation).

The global assessment of efficacy (overall pain control) was assessed on D7 after surgery by use of a 4-point scale (0=excellent, 1=good, 2=fair, and 3=poor).

From day D1 to D7, owners daily assessed the dogs' wellbeing using scales for:

Demeanour (0=normal; 1=slightly modified; 2=moderately modified; 3=markedly modified and 4=severely modified).

Mobility (0=normal; 1=slightly impaired; 2=moderately impaired; 3=markedly impaired and 4=severely impaired).

Quality of analgesia as very satisfactory (=1); satisfactory (=2); not very satisfactory (=3); not at all satisfactory (=4).

Blood samples were collected from all animals before inclusion (≤D-2), for routine pre-surgery blood profile. Potential adverse effects related to the products were also recorded.

Statistical Analysis was performed by use of commercially available software. All analyses used a two-sided significance level $\alpha=0.05$. Demographic and baseline data were compared between groups using the Mann-Whitney U test or Fisher exact probability test. The area under the curve (AUC) was calculated for observable pain during the initial 24 hours, and it was considered as the primary efficacy variable and analysed with an ANOVA. SFGCMPS total score and the other secondary efficacy variables were also analysed using repeated measures analysis of variance with treatment, time and interaction "treatment"דtime" as fixed effects and animal (nested in treatment) as random effect. Additionally, comparisons between treatments at each time point were also performed by the Mann-Whitney U test.

The statistical analysis confirmed both groups were balanced for the main variables before surgery (see Table 3).

TABLE 3

Basal distribution of the demographic parameters of dogs in each group.

| | CG | TG | P |
|---|---|---|---|
| Body weight (kg) | 20.67 | 25.28 | >0.05 N.S. |
| Age (years) | 5.96 | 4.41 | >0.05 N.S. |
| Surgery duration (min) | 89.88 | 88.12 | >0.05 N.S. |
| SFGCMPS | 2.94 | 3.62 | >0.05 N.S. |
| Pain at rest | 0.67 | 0.77 | >0.05 N.S. |
| Pain at gentle manipulation | 1.64 | 1.52 | >0.05 N.S. |
| Level of inflammation | 2.31 | 2.29 | >0.05 N.S. |
| Males | 8 | 6 | >0.05 N.S. |
| Females | 8 | 10 | |

No significant differences were detected in the primary efficacy variable SFGCMPS (AUC). The CG obtained an average value of 100.31±46.14 and the TG a value of 95.50±57.70 (p=0.7962). When SFGCMPS was analysed by repeated measure again no statistically significant differences were detected (p=0.3832).

Figure 3:
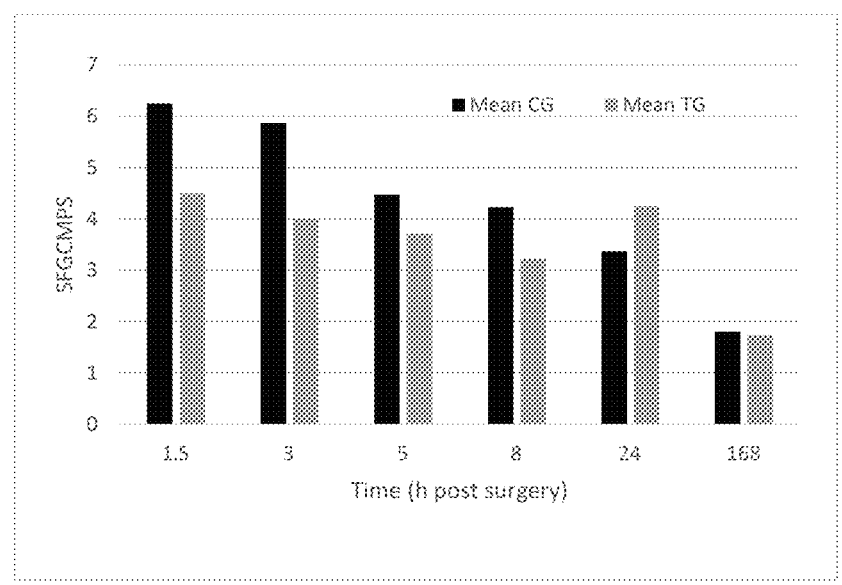
FIG. 3. Evolution of average SFGMPS total scores at the different time points after orthopaedic surgery in dogs treated with E-6087 (Treatment group—TG) or meloxicam (control group—CG).

When SFGCMPS was analysed at each time point most values were lower for the TG (see FIG. 3). However, no statistically significant differences were reached at any time point.

Figure 4:
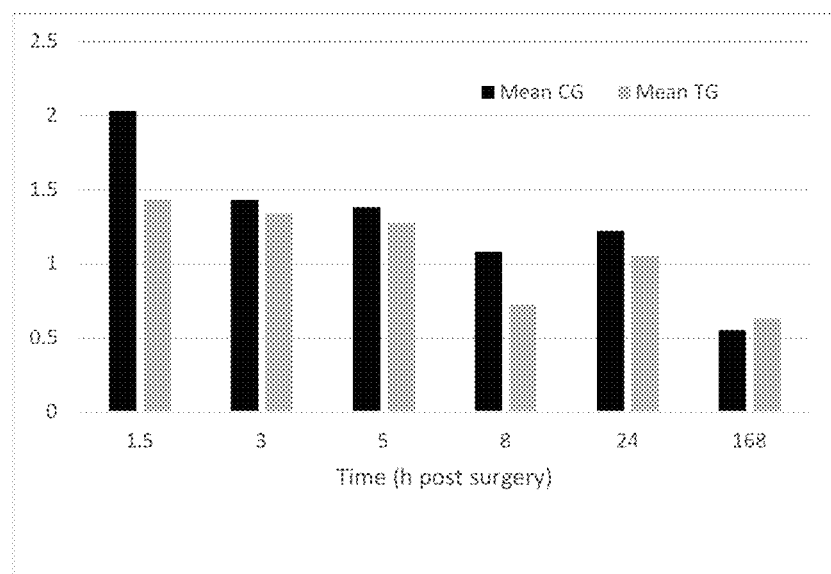
FIG. 4. Evolution of average pain at rest at the different time points after orthopaedic surgery in dogs treated with E-6087 (TG) or meloxicam (CG).
Figure 5:
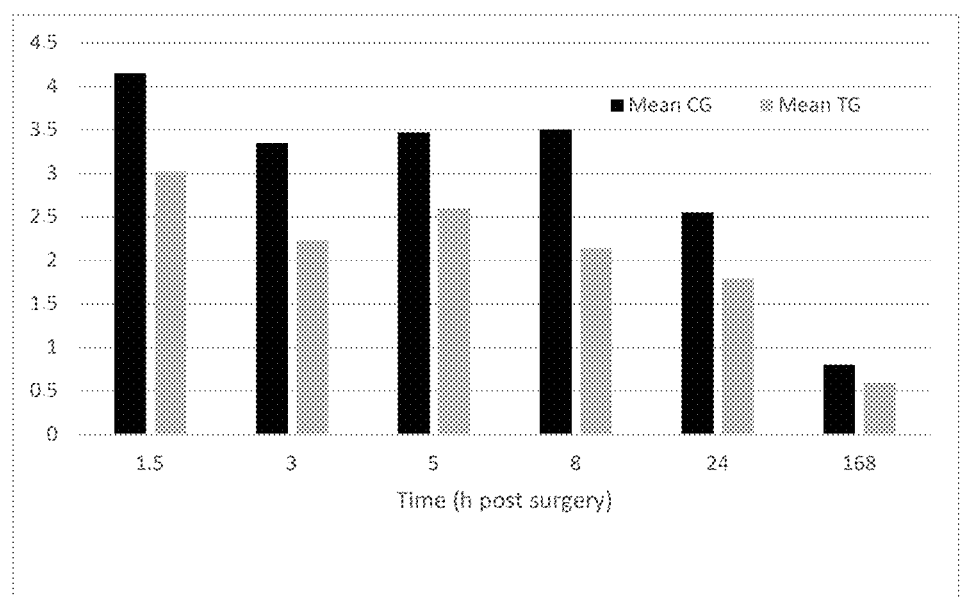
FIG. 5. Evolution of average pain at gentle palpation at the different time points after orthopaedic surgery in dogs treated with E-6087 (TG) or meloxicam (CG).
Figure 6:
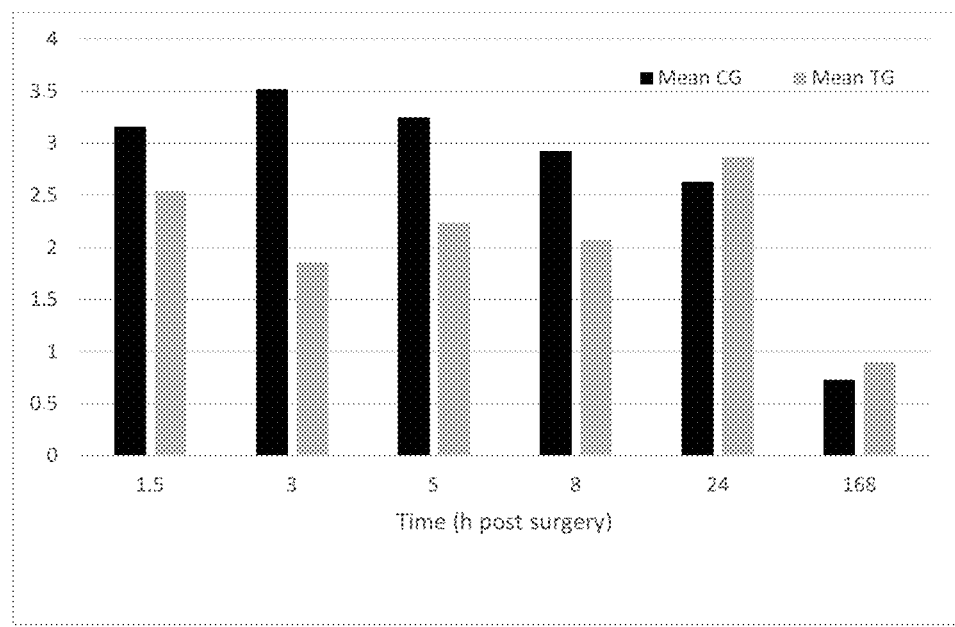
FIG. 6. Evolution of average level of inflammation at the different time points after orthopaedic surgery in dogs treated with E-6087 (TG) or meloxicam (CG).

Same results were obtained when analysing the other secondary efficacy variables pain at rest (FIG. 4) and pain after gentle manipulation (FIG. 5). For the level of inflammation (FIG. 6) statistically significant differences were observed at 3 h were E-6087 showed lower values (p=0.025).

Figure 7:
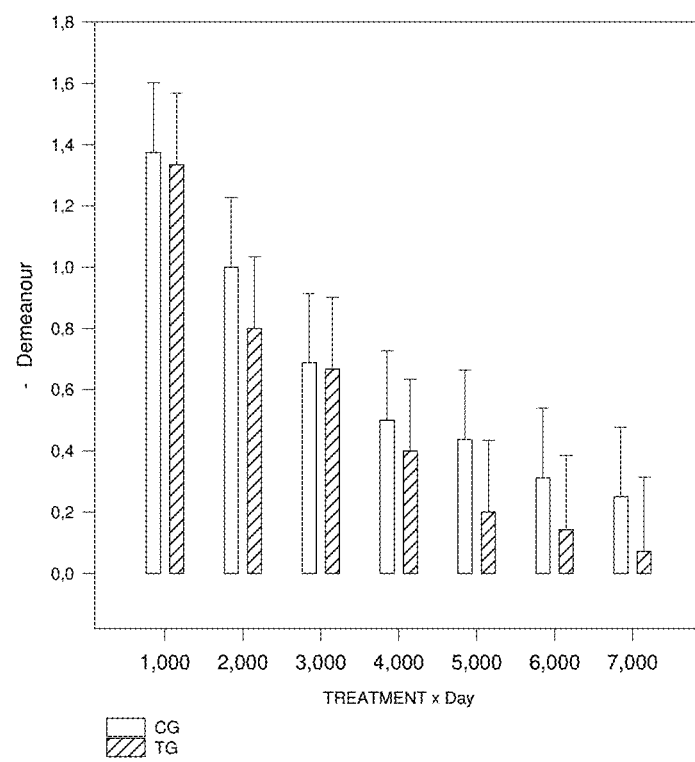
FIG. 7. Evolution of demeanour at the different time points after orthopaedic surgery in dogs treated with E-6087 (TG) or meloxicam (CG).
Figure 8:
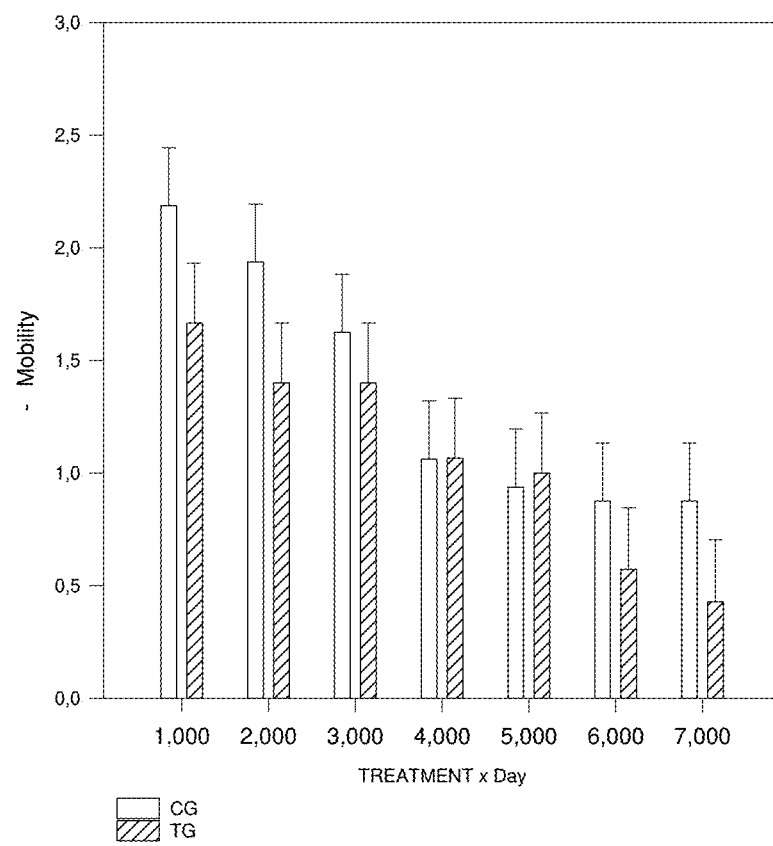
FIG. 8. Evolution of Mobility at the different time points after orthopaedic surgery in dogs treated with E-6087 (TG) or meloxicam (CG).
Figure 9:
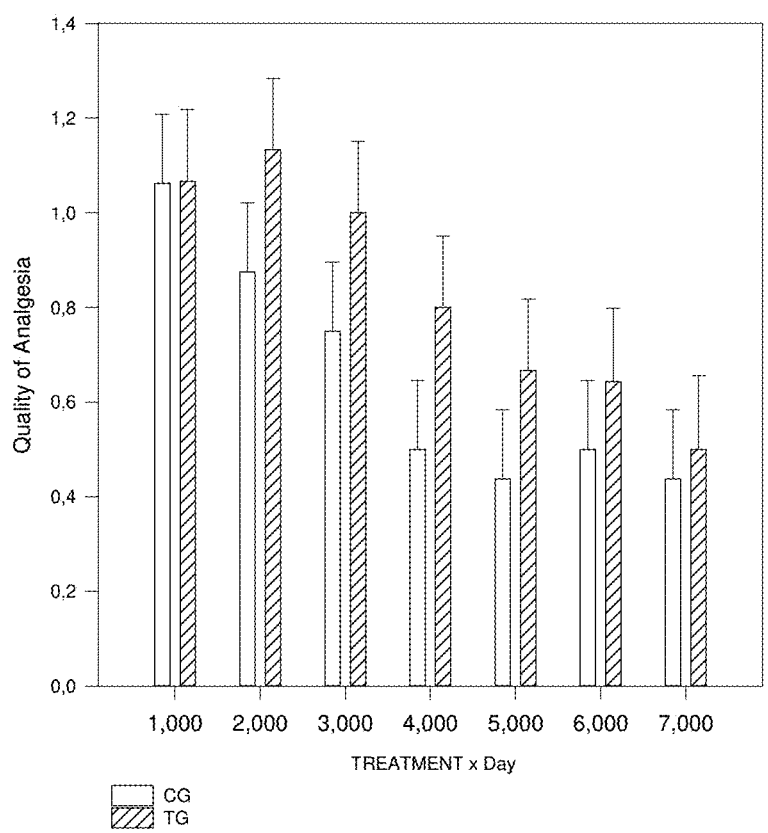
FIG. 9. Evolution of the quality of analgesia at the different time points after orthopaedic surgery in dogs treated with E-6087 (TG) or meloxicam (CG).

No differences were detected on the assessment of global efficacy on D7 (p=0.7879), or on the owners' assessment of the dogs' wellbeing (See FIGS. 7-9).

It is concluded according to the examples that the administration of an oral dose of enflicoxib preferably prior to orthopaedic surgery offers a similar level of analgesia and anti-inflammatory effect as the reference product meloxicam administered daily at its recommended therapeutic posology.

REFERENCES

1—Mathews K A. Pain assessment and general approach to management. Vet Clin North Am Small Anim Pract. 2000 July; 30(4):729-55, 2—Pascoe P J. Perioperative pain management. Vet Clin North Am Small Anim Pract. 2000 July; 30(4):917-32.

3—Bonnet F, Marret E. Influence of anaesthetic and analgesic techniques on outcome after surgery. Br J Anaesth, 2005 July; 95(1):52-8. doi: 10.1093/bja/aei038. Epub 2004

4—Wagner A E, Worland G A, Glawe J C, Hellyer P W. Multicenter, randomized controlled trial of pain-related behaviors following routine neutering in dogs, J Am Vet Med Assoc. 2008 Jul. 1; 233(1):109-15.

5—Lamont L A, Mathews K A. Opioids, non-steroidal anti-inflammatories and analgesic adjuvants. In: Tranquilli W J, Thurmon J C, Grimm K A, eds. Lumb and Jones' Veterinary Anesthesia and Analgesia. 4th edn. Blaekwell Publishing, 2007:241-72

6—Budsberg S C, Cross A R, Quandt J E, Pablo L S, Runk A R. Evaluation of intravenous administration of meloxicam for perioperative pain management following stifle joint surgery in dogs. Am J Vet Res. 2002 November; 63(11):1557-63. doi: 10.2460/ajvr.2002.63.1557. PMID: 12428667, 7—Martins T L, Kahvegian M A, Noel-Morgan J, Leon-Román M A, Otsuki D A, Fantoni D T. Comparison of the effects of tramadol, codeine, and ketoprofen alone or in combination on postoperative pain and on concentrations of blood glucose, serum cortisol, and serum interleukin-6 in dogs undergoing maxillectomy or mandibulectomy. Am J Vet Res. 2010 September; 71(9): 1019-26.

8—Kerr, C. (2016) Pain management I: systemic analgesics In: BSAVA Manual of Canine & Feline Anaesthesia & Analgesia. $2^{nd}$ ed. Eds C. J. Seymour and T. Duke-Novakowski. BSAVA, Gloucester, UK. Chapter 10, pp 124-142

9—Gruet P, Seewald W, King J N. Evaluation of subcutaneous and oral administration of robenacoxib and meloxicam for the treatment of acute pain and inflammation associated with orthopedic surgery in dogs, Am J Vet Res. 2011 February; 72(2):184-93, dol:10.2460/ajvr.72.2.184, PMID: 21281192.

10—Friton C, Thompson C M, Karathovska D, King S, King J N. Efficacy and safety of oral robenacoxib (tablet) for the treatment of pain associated with soft tissue surgery in client-owned dogs. BMC Vet Res. 2017 Jun. 26; 13(1):197.

11—Grandemange E, Fournel S, Woehrlé F. Efficacy and safety of cimicoxib in the control of perioperative pain in dogs. J Small Anim Pract. 2013 June; 54(6):304-12.

12—Ramirez J, Barthélémy N, Noël S, Claeys S, Etchepareborde S, Farnir F, Balligand M. Complications and outcome of a new modified Maquet technique for treatment of cranial cruciate ligament rupture in 82 dogs. Vet Comp Orthop Traumatol. 2015; 28(5):339-46.

13—Reid J, Nolan A M, Hughes J M L, et al. Development of the short-form Glasgow Composite Measure Pain Scale (CMPSSF) and derivation of an analgesic intervention score. Animal Welfare 2007; 16 (S):97-104.

The invention claimed is:

1. A method of treating or preventing pain and inflammation associated to surgery in a mammal, said method comprising:

administering to said mammal a compound of formula (I) at a single dose:

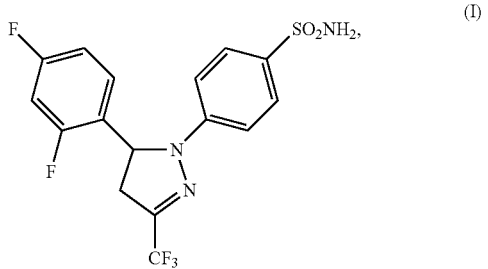 [SMILES: NS(=O)(=O)c1ccc(N2N=C(C(F)(F)F)CC2c2ccc(F)cc2F)cc1]

wherein the mammal is a dog.

2. The method according to claim 1, wherein said single dose administering comprises administering the compound at a single dose from 1 to 10 mg/kg of body weight.

3. The method according to claim 2, wherein the dose is from 4 to 8 mg/kg of body weight.

4. The method according to claim 2, wherein the dose is 4 mg/kg or 8 mg/kg of body weight.

5. The method according to claim 1, wherein said surgery is a soft tissue surgery.

6. The method according to claim 1, wherein said surgery is an orthopaedic surgery.

7. The method according to claim 1, wherein said surgery is a neurosurgery.

8. The method according to claim 1, wherein said surgery is a dental surgery.

9. The method according to claim 1, wherein said surgery is an oncologic surgery.

10. The method according to claim 1, wherein said surgery is an ear surgery.

11. The method according to claim 1, wherein said surgery is a skin tumour removal surgery.

12. The method according to claim 2, wherein the single dose is administered at least 2 days before the surgery, 1 day before the surgery, the same day of the surgery or one day after the surgery.

13. The method according to claim 1, wherein the compound is included in a composition with at least one pharmaceutically acceptable excipient.

14. The method according to claim 1, wherein the method treats said pain and inflammation.

15. The method according to claim 1, wherein the method prevents said pain and inflammation.

16. The method according to claim 1, wherein the method treats and prevents said pain and inflammation.

* * * * *